(12) United States Patent
Sundararajan et al.

(10) Patent No.: US 7,115,230 B2
(45) Date of Patent: Oct. 3, 2006

(54) HYDRODYNAMIC FOCUSING DEVICES

(75) Inventors: Narayanan Sundararajan, San Francisco, CA (US); Andrew Berlin, San Jose, CA (US)

(73) Assignee: Intel Corporation, Santa Clara, CA (US)

( * ) Notice: Subject to any disclaimer, the term of this patent is extended or adjusted under 35 U.S.C. 154(b) by 203 days.

(21) Appl. No.: 10/609,227

(22) Filed: Jun. 26, 2003

(65) Prior Publication Data

US 2004/0266022 A1    Dec. 30, 2004

(51) Int. Cl.
  *B01L 3/02* (2006.01)
(52) U.S. Cl. .................. 422/100; 422/103; 436/63
(58) Field of Classification Search ............... 422/100, 422/103; 436/63; 137/89, 98
  See application file for complete search history.

(56) References Cited

U.S. PATENT DOCUMENTS

| | | | |
|---|---|---|---|
| 3,871,770 A | | 3/1975 | von Behrens et al. |
| 5,858,187 A | | 1/1999 | Ramsey et al. |
| 5,972,710 A | | 10/1999 | Weigl et al. |
| 6,067,157 A | | 5/2000 | Altendorf |
| 6,120,666 A | * | 9/2000 | Jacobson et al. ............ 204/452 |
| 6,159,739 A | | 12/2000 | Weigl et al. |
| 6,382,228 B1 | | 5/2002 | Cabuz et al. |
| 6,408,878 B1 | | 6/2002 | Unger et al. |
| 6,454,945 B1 | | 9/2002 | Weigl et al. |
| 6,488,872 B1 | | 12/2002 | Beebe et al. |
| 6,506,609 B1 | | 1/2003 | Wada et al. |
| 6,749,814 B1 | * | 6/2004 | Bergh et al. ................. 422/130 |
| 2003/0040119 A1 | * | 2/2003 | Takayama et al. ............ 436/63 |
| 2003/0054558 A1 | * | 3/2003 | Kurabayashi et al. ......... 436/63 |

OTHER PUBLICATIONS

G. M. Whitesides and A. D. Stroock, "Flexible Methods for Microfluids". Physics Today Jun. 2001 [online]. [retrieved on Jan. 2, 2003] Retrieved from the Internet: http://www.physicstoday.org/pt/vol-54/iss-6/p42.html. pp. 1-8.
J. R. Anderson, et al., "Fabrication of Topologically Complex Three-Dimensional Microfluidic Systems in PDMS by Rapid Prototyping".*Analytical Chemistry*, vol. 72, No. 14, Jul. 15, 2000. pp. 3158-3164.
Y. Xia, G. M. Whitesides, Soft Lithography, *Agnew. Chem. Int. Ed* . 37, 551-575 (1998).
D.C. Duffy, J. C. McDonald, O.J.A. Schueller, G. M. Whitesides, *Analytical Chemistry* vol. 70, No. 23, Dec. 1, 1998. pp. 4974-4984.

* cited by examiner

*Primary Examiner*—Jill Warden
*Assistant Examiner*—Natalia Levkovich
(74) *Attorney, Agent, or Firm*—DLA Piper Rudnick Gray Cary US LLP

(57) ABSTRACT

A micro-fluidic device containing a micro-fluidic inlet channel to convey a process flow, a plurality of micro-fluidic focusing channels to each convey one of a plurality of focusing flows, a focusing manifold coupled with the inlet channel at an inlet port thereof and with the plurality of focusing channels at a plurality of focusing channel ports thereof to focus the process flow by contacting and hydrodynamically impacting at least three sides of the process flow with the focusing flows, and a micro-fluidic outlet channel coupled with the focusing manifold at an outlet channel port to convey the combined focused process flow and focusing flow from the focusing manifold.

35 Claims, 9 Drawing Sheets

HYDRODYNAMIC FOCUSING DEVICES

BACKGROUND

1. Field

Embodiments of the invention relate generally to micro-fluidic devices, and more particularly, to micro-fluidic hydrodynamic focusing devices.

2. Background

Various hydrodynamic focusing systems, their properties, and their uses have been discussed in the patent literature. Several examples are provided in U.S. Pat. No. 5,858,187 issued Jan. 12, 1999 to Ramsey et al., U.S. Pat. No. 6,120,666 issued Sep. 19, 2000 to Jacobson et al., and U.S. Pat. No. 6,159,739 issued Dec. 12, 2000 to Weigl et al., and U.S. Pat. No. 6,506,609 issued Jan. 14, 2003 to Wada et al. The above-identified patents are not admitted to be prior art with respect to the invention by their mention in the background.

BRIEF DESCRIPTION OF THE SEVERAL VIEWS OF THE DRAWINGS

The invention may best be understood by referring to the following description and accompanying drawings that are used to illustrate embodiments of the invention. In the drawings.

DETAILED DESCRIPTION

In the following description, numerous specific details are set forth. However, it is understood that embodiments of the invention may be practiced without these specific details. In other instances, well-known circuits, structures and techniques have not been shown in detail in order not to obscure the understanding of this description.

I. Introduction

Figure 1:
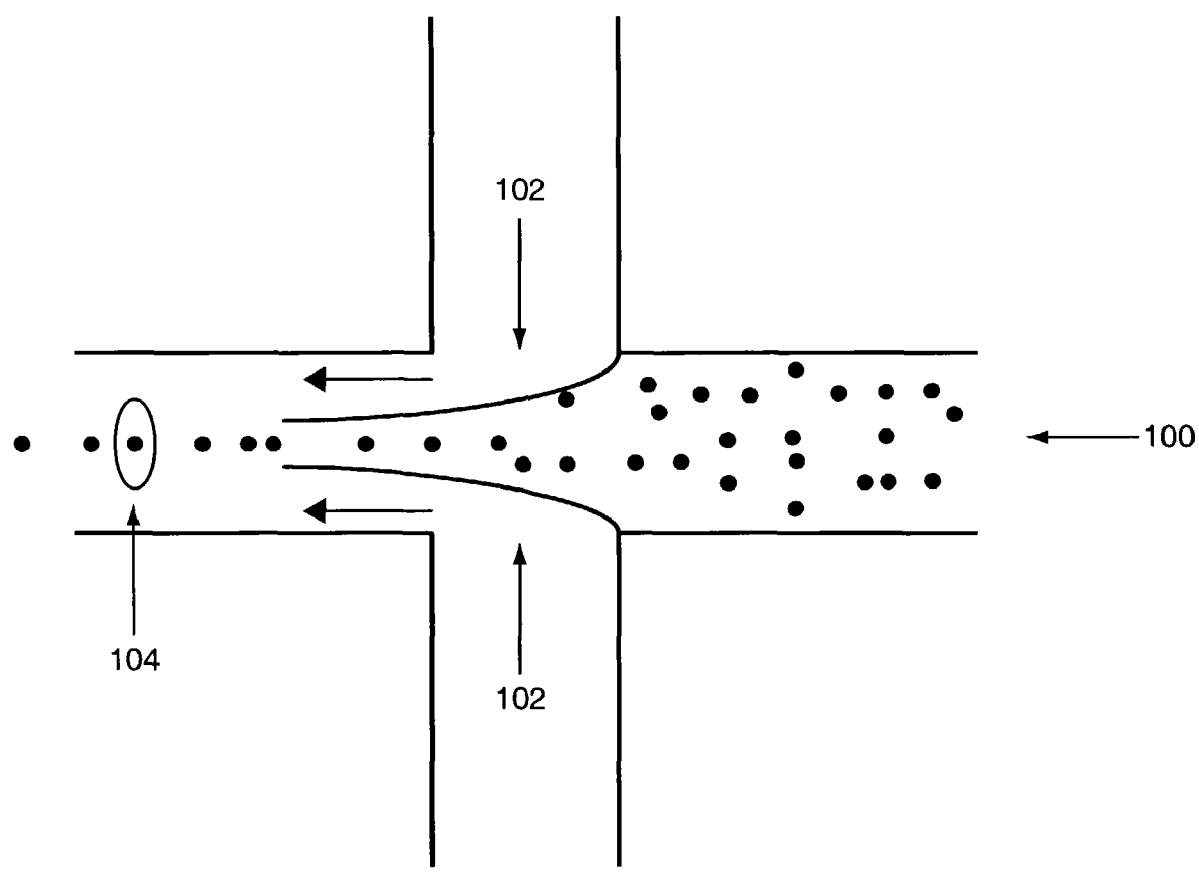
FIG. 1 shows an approach for focusing cells in a micro-scale system by simultaneous flow from two side channels into a main channel through which the cells are being flowed.

U.S. Pat. No. 6,506,609, issued Jan. 14, 2003, to Wada et al., discusses in part focusing of micro-particles in micro-fluidic systems. FIG. 1 shows the approach represented in FIG. 1A of the '609 patent for focusing cells 100 in a micro-scale system by simultaneous flow from two side channels into a main channel through which the cells are being flowed. Cells 100 (or other particles) are typically flowed from the main micro-channel into the cross-junction and focused by introducing hydrodynamic flows 102 from the two orthogonal micro-channels. Non-orthogonal micro-channels may also be used. The cells 100 are optionally constrained to the center of a detection micro-channel downstream from the two orthogonal micro-channels by hydrodynamic flows 102 introduced from both sides as cells 100 pass through detector 104. One limitation of the system shown in FIG. 1 is that there is no focusing or narrowing of the flow containing the cells in the vertical direction orthogonal to the cross-junction and the cells may contact the upper and lower surfaces of the detection micro-channel.

II. Exemplary Hydrodynamic Focusing Systems

Figure 2A:
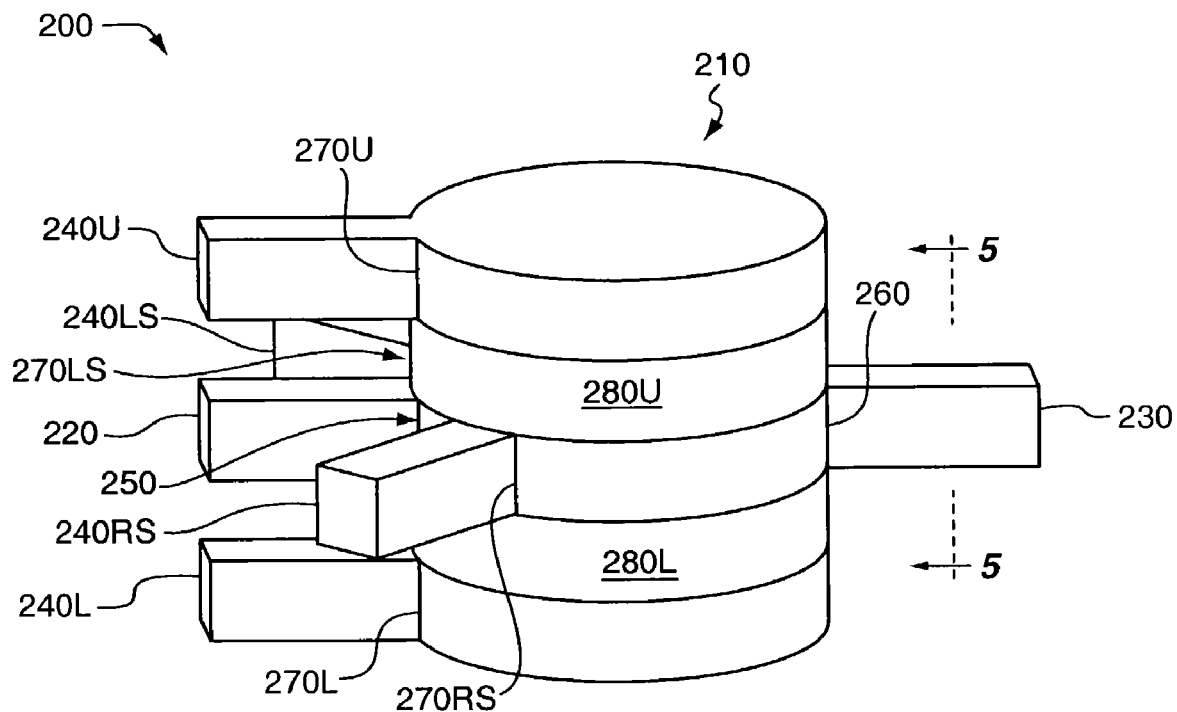
FIG. 2A shows a front perspective view of a hydrodynamic focusing device, according to an embodiment of the invention.

FIG. 2A shows a front perspective view of a hydrodynamic focusing device 200, according to one embodiment of the invention. The hydrodynamic focusing device contains a micro-fluidic inlet channel 220 to convey a process flow and a plurality of micro-fluidic focusing channels 240 (240LS, 240RS, 240U, and 240L) to each convey one of a plurality of focusing flows. The hydrodynamic focusing device further contains a micro-fluidic focusing manifold 210 coupled with the inlet channel 220 at an inlet channel port 250 and with the plurality of focusing channels 240 at a plurality of focusing channel ports 270 (270LS, 270RS, 270U, and 270L). The hydrodynamic focusing device focuses the process flow by contacting and hydrodynamically impacting at least three sides of the process flow with the focusing flows. In the illustrated embodiment four sides, for example a left side, a right side, a top side, and an underside, are contacted and focused inward. In an alternate embodiment any one of the four focusing channels may be omitted, such as channel 240U, and the process flow focused by contacting three sides of the process flow with the focusing flows. Still further the hydrodynamic focusing device includes a micro-fluidic outlet channel 230 coupled with the focusing manifold 210 at an outlet channel port 260 to convey the combined focused process flow and focusing flow from the focusing manifold.

In the illustrated hydrodynamic focusing device, the process flow conveyed through the inlet channel may be confined and focused using four focusing flows conveyed respectively through a first micro-fluidic focusing channel 240LS on a first side of the inlet channel (on a left side when facing downstream the inlet channel), a second micro-fluidic focusing channel 240RS on a second side of the inlet channel (a right side), a third upper micro-fluidic focusing channel 240U over the inlet channel, and a fourth lower micro-fluidic focusing channel 240L under the inlet channel. It should be noted that terms such as "top", "bottom", "upper", "lower", "vertical", "horizontal", and the like, are used herein only to facilitate the description of the structure of the illustrated micro-fluidic device "as viewed". It will be evident that the devices may be used in a variety of orientations including tilted orientations. The first and the second focusing channels are on opposite sides of the inlet channel, and in the illustrated embodiment are angled relative to the inlet channel so that focusing fluids conveyed through these channels impacts with the process fluid conveyed through the inlet channel at an angle. The angle in the illustrated embodiment is sub-orthogonal and approximately 45°, although this is not required, and other angles in a range between approximately 5° to 90° may also optionally be employed. Smaller angles may be more difficult to fabricate, depending on the channel dimensions, although they may also optionally be employed. Exemplary sub-orthogonal angles are approximately 15°, 30°, 45°, 60°, and 75°. In these sub-orthogonal angles at least a portion of a focusing flows momentum is aligned with the process flow. The angles of the first and the second focusing channels will often be approximately equal so that the momentum components of these focusing flows, which are not aligned with the momentum of the process flow, tend to negate.

The third and the fourth focusing channels approach the focusing manifold from the same side as the inlet channel. As shown, the third upper micro-fluidic focusing channel 240U may be substantially vertically aligned over the inlet channel 220, and a fourth lower micro-fluidic focusing channel 240L may be substantially vertically aligned under the inlet channel 220. The substantial alignment may offer the advantage that a large component or vector of the flow may be aligned with the inlet flow. This may also help reduce deflecting or rotating the process flow. It will be appreciated that precise alignment is not a requirement of the invention. If the upper and lower focusing channels have angles relative to the inlet channel that are less than approximately 45°, a majority component or vector of the flow may be aligned with respect to the inlet flow. Accordingly, not greater than approximately 45°, 30°, or especially 15° may be employed in order to achieve the benefit associated with the illustrated embodiment. In this embodiment substantially aligned means angles not greater than approximately 15° relative to the inlet channel. As shown the first and the second focusing channels are coplanar with the micro-fluidic inlet channel in a horizontal plane, whereas the third and the fourth focusing channels are not coplanar with the horizontal plane (they are either above or below the horizontal plane).

As shown, the outlet channel may be on an opposite side of the focusing manifold as the inlet channel, and may be substantially aligned opposite to the inlet channel. The substantial alignment of the inlet and outlet channels may be appropriate in order to avoid significantly changing the direction of the process fluid within the focusing manifold. In this embodiment, substantially aligned means angles not greater than approximately 15° relative to the inlet channel. Small angles, often less than 45°, may be appropriate in alternate implementations.

The micro-fluidic channels represent micro-sized fluid passages that may have a cross-sectional dimension e.g., channel width, channel height, channel diameter, etc. that may be not greater than approximately one millimeter (mm, one-thousandth of a meter, also 1000 µm). In various embodiments the cross-sectional dimension may be not greater than approximately 500 micrometers (µm, one millionth of a meter), 200 µm, 100 µm, 50 µm, or 10 µm. To help put these lengths in proper perspective, the cross-sectional diameter of a human hair is often on the order of 100 µm. The invention is not limited to any known minimum cross-sectional dimension for the channels. In various embodiments the cross-sectional dimension may be greater than approximately 0.001 µm (1 nm), greater than approximately 0.01 µm (10 nm), or greater than approximately 0.1 µm (100 nm). The optimal dimension of the channel may depend upon the characteristics of the fluids and/or particles to be conveyed therein. An exemplary micro-fluidic channel which may be used for one or more of an inlet, outlet, or focusing channel, may comprise a rectangular channel having a channel width of approximately 100 µm and a channel height of approximately 50 µm. The rectangular shape and specific dimensions are not required. These miniaturized channels are often useful for handling small sized samples and allow many channels to be constructed in a small substrate, although this is not a requirement. As will be discussed further below, these minute sized channels promote laminar flow that is conducive to hydrodynamic focusing as discussed herein. There is no known minimum or maximum length for the channels. Commonly the channel lengths are at least several times their width and not more than several centimeters.

The focusing manifold 210 represents a junction configured to receive flows introduced through the channels, focus the process flow by contacting and hydrodynamically impacting all four sides of the process flow with focusing flow, and remove the focused process flow and focusing flow through the outlet channel. The manifold includes an inlet port 250 to receive a process flow conveyed through the inlet channel, an outlet port 260 to provide a focused process flow to the outlet channel, and a plurality of focusing channel ports 270 (270LS, 270RS, 270U, and 270L) each corresponding to one of the plurality of focusing channels to receive focusing flows. Specifically, the illustrated focusing manifold includes a first focusing channel port 270LS (not visible) on the first side of the inlet channel (a left side) for receiving a focusing flow conveyed through the first focusing channel, a second focusing channel port 270RS on a second side of the inlet channel (a right side) for receiving a focusing flow conveyed through the second focusing channel, a third focusing channel port 270U over the inlet channel for receiving a focusing flow conveyed through the third focusing channel, and a fourth focusing channel port 270L under the inlet channel for receiving a focusing flow conveyed through the fourth focusing channel. As shown, the third port 270U may be substantially vertically aligned over the inlet channel and the fourth port 270L may be substantially vertically aligned under the inlet channel.

The particular illustrated focusing manifold has a housing or enclosure defining a void having a shape of an upright cylinder and an enlarged void volume. The enlarged void volume is employed to facilitate alignment in a method of forming the focusing manifold by stacking a plurality of substrates having void portions formed therein over one another to complete the void. The enlarged void volume may facilitate mutual alignment of the void portions. The cylindrical shape may be readily fabricated and lacks extremities, such as corners, which may promote stagnant zones, although this shape is not required, and other focusing manifolds may have spherical, cubic, or other shapes. Often a void volume not greater than approximately 0.1 mm$^3$ (cubic millimeters) may be appropriate to reduce diffusion and any potential gravity settling in the focusing manifold. For example, the illustrated manifold may have a diameter of approximately 250 µm, a height of approximately 250 µm, and a corresponding volume of approximately 0.01 mm$^3$. The inventors have found that such diameters may be readily aligned when a "membrane-sandwich" fabrication approach is employed to form the focusing manifold with the use of a relatively unsophisticated alignment system, such as manual alignment with a stereo microscope. More sophisticated alignment methods are available, such as using optical recognition software and alignment marks, as employed in the semiconductor manufacturing arts. Smaller dimensions may be employed, as desired, if a more sophisticated alignment system is used, or if vertical alignment is not required for forming the manifold. In such cases, exemplary manifolds may have a void volume not greater than approximately 0.01 mm³, 0.001 mm³, or less. If a sophisticated alignment tool is used, or if alignment is not required, an enlarged void volume may be avoided entirely, and a manifold may have dimensions approximately the same as channel dimensions.

Figure 2B:
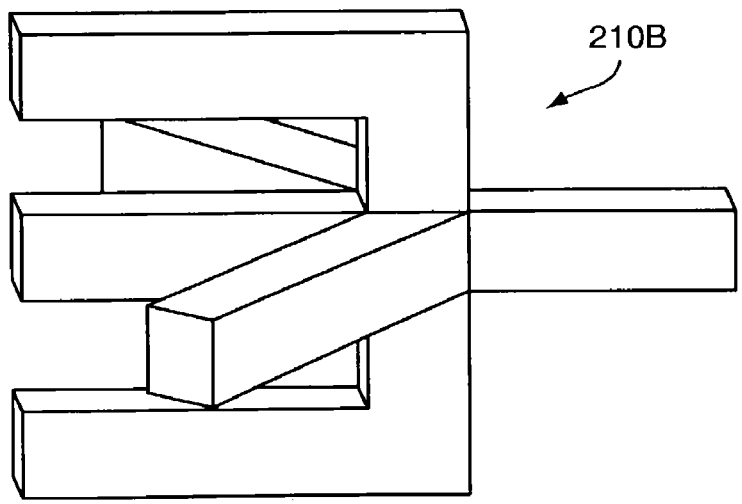
FIG. 2B shows a front perspective view of a hydrodynamic focusing device having a small-volume focusing manifold, according to an embodiment of the invention

As one example, FIG. 2B shows a front perspective view of a hydrodynamic focusing device 200B having a small volume focusing manifold 210B, according to an embodiment of the invention. The small volume focusing manifold 210B may have a volume that is not greater than approximately 0.001 mm³. As illustrated, the focusing manifold may have a shape of a rectangular solid, a width about the same as that of a 100 μm width inlet channel, a length about the same as that of a 100 μm width side focusing channel, and a height about the same as that of a 50 μm high inlet channel, and a corresponding volume of approximately 0.0005 mm³. Alternatively the focusing system dimensions do not need to be equal to, but may be proportional or otherwise related to channel dimensions.

Referring again to FIG. 2A, as shown the focusing manifold may contain a plurality of optional spacing volumes 280. The illustrated spacing volumes include a first upper spacing volume 280U between the third upper port 270U for the upper focusing channel and the inlet port 250, and a second lower spacing volume 280L between the fourth lower port 270L for the lower focusing channel and the inlet port 250. The spacing volumes may help to facilitate fabrication when alignment is employed in forming the manifold. Also, the spacing volumes may help to slow the flow of the focusing fluids in the manifold and may help to isolate the process flow from the momentum of the third and fourth focusing flows, and from potential fluctuations in the momentum of these flows, and thereby reduce mixing. The amount of mixing in the manifold is expected to be quite small. The spacing volumes are optional and may be omitted from the manifold. As shown, the spacing volumes may comprise cylindrical portions having diameters that are substantially the same as the diameters of other cylindrical portions of the focusing manifold and having heights that are substantially the same as the heights of the micro-fluidic channels. As an example, the spacing volumes may comprise cylindrical portions or sections having diameters of approximately 250 μm and heights of approximately 50 μm. Alternatively the spacing volumes may have other shapes, cross-sectional dimensions, and heights. Often the height may be less than approximately 100 μm or less than approximately 75 μm. As yet another option the spacing volumes may be omitted and the upper focusing channel and lower focusing channel may respectively be formed in the superjacent and subjacent levels relative to the level containing the inlet and outlet channels.

An embodiment of the invention relates to a method for focusing a process flow in a hydrodynamic focusing device as described herein. The method may comprise introducing the process flow to a focusing manifold through a micro-fluidic inlet channel and concurrently introducing a plurality of focusing flows to the focusing manifold through a plurality of micro-fluidic focusing channels. Then the process flow may be focused by impacting it on all four sides thereof with the plurality of focusing flows in the focusing manifold. Next the focused process flow may be removed from the focusing manifold through a micro-fluidic outlet channel.

With reference to FIG. 2A, introducing the plurality of focusing flows may include introducing a first focusing flow to the focusing manifold through the first focusing channel and the first port, introducing a second focusing flow to the focusing manifold through the second focusing channel and the second port, introducing a third focusing flow to the focusing manifold through the third focusing channel and the third port, and introducing a fourth focusing flow to the focusing manifold through the fourth focusing channel and the fourth port. The fluids may be introduced into the inlets using a variety of fluid movement devices or pumps that are known in the arts. Suitable pumps include among others syringe pumps, electroosmosis pumps, thermal pumps, and surface tension pumps. The fluids may be introduced as steady streams or flows, or as discrete pulses. The flow rates and or the pressures in the different channels may be the same or different.

In performing the hydrodynamic focusing as described herein a non-turbulent, unmixed, or laminar flow may be appropriate, inasmuch as any turbulent flow may lead to undesired mixing. The Reynolds number is a well-known ratio of inertial forces to viscous forces often used to specify whether the flow is laminar or turbulent. In laminar flow, when the Reynolds number is low, such as not greater than 1, the viscous forces are larger than the inertial forces, and the fluid moves with smooth streamlines that are substantially parallel to the channel walls. True laminar flow lacks eddies where the streamlines break into complex or chaotic spirals or other random or turbulent fluctuations that cause mixing in the direction normal to flow. The use of the term laminar flow herein encompasses potentially limited amounts of turbulence or localized turbulence consisting of a few eddies at the point where the focusing fluids impact the process fluid. A flow in a channel may have a non-turbulent, unmixed, or laminar flow and may be characterized by a Reynolds number that is either not greater than approximately 1000, 100, 10, 1, 0.1, or 0.01. Achieving such non-turbulent flow is not difficult at flow rates that are commonly employed in micro-fluidic structures since the small dimensions and close proximity of the walls and other no-flow boundaries in such micro-fluidic structures tend to promote laminar flow. When the process and focusing flows have such non-turbulent flow they move nearly parallel to one other within the channel without becoming significantly mixed in the direction normal to their flow due to turbulence. The flows may experience limited concentration-driven diffusional mixing in the direction normal to their boundary.

As the flows are received within the focusing manifold all four sides of the process flow may be impacted with and confined and focused by the combined focusing flow. In the device illustrated in FIG. 2A the four focusing flows are received into the focusing manifold around all four sides of the process flow. In such a device focusing may include impacting a first side of the process flow with the first focusing flow, impacting a second side of the process flow with the second focusing flow, impacting a top of the process flow with the third focusing flow, and impacting a bottom of the process flow with the fourth focusing flow. In the type of laminar flow that occurs in micro-fluidic devices the focusing and process flows do not mix significantly at impact but instead come into alignment with discrete interfaces and move together as separate and distinct flows through the manifold.

At impact the focusing flows exert forces, sometimes referred to as hydrodynamic forces, on the surfaces of the process flow, due to their motion. The hydrodynamic forces or pressures exerted by the focusing flows on the process flow compress the process flow within the focusing manifold and outlet channel into a focused process flow or stream that has a smaller cross sectional area. The pressures applied by the combined focusing flow drive the extremities of the process flow inward toward the center from all sides and shrink the cross section. The focusing flows delivered through the first and second focusing channels compress and focus the process flow in the lateral direction from both sides whereas the focusing flows delivered through the third and fourth focusing channels compress and focus the process flow in the vertical direction from both sides. The combined focusing flow compresses and focuses the process flow in the vertical and lateral directions inward from each of its four sides. The amount of focusing increases with increasing applied hydrodynamic force (i.e., with increasing flow rates in the focusing channels). Increasing the focusing flow rate may increase the amount of focusing and decreased the focusing flow rate may decrease the amount of focusing. The amount of focusing also depends upon, and varies inversely with, the cross-sectional area of the outlet channel available for flow. Increasing the cross-sectional area may decrease the amount of focusing and decreasing the cross-sectional area may increase the amount of focusing. By varying these parameters the amount of focusing may be varied from a very small amount to a very large amount of focusing. When the focusing fluids delivered through the different channels have similar hydrodynamic forces, for example similar flow rates, the amount of compression or focusing in the vertical and lateral directions may be similar. Optionally different hydrodynamic forces may be provided to the various focusing flows to modify the amount of compression and focusing along the different sides of the process flow and/or to control different amounts of hydrodynamic focusing in the vertical and lateral directions.

The combined focusing flow completely surrounds and spatially confines the centralized process flow at or near the center of the focusing manifold. The focusing flow separates the process flow from the walls of the focusing manifold including from upper and lower walls. The centralized process flow and the surrounding focusing flow move from their respective inlet ports toward the outlet port. Laminar flow with minimal if any turbulence may be maintained within the focusing manifold to minimize mixing. The focusing manifold may be designed with the outlet channel substantially opposite the inlet channel to allow the process flow to proceed from its inlet directly across the focusing manifold toward the outlet channel with a non-tortuous flow path. The process flow and its associated surrounding focusing flow pass from the manifold to the outlet channel via the outlet port. The combined focusing flow completely surrounds and spatially confines the centralized process flow at or near the center of the outlet channel. The combined focusing flow separates the centralized process flow from the channel walls. The shielding of the process flow from the channel walls may be desired in numerous situations including when the process flow contains a component that may adhere to or otherwise be incompatible with the channel walls.

The focused process flow has a smaller cross-sectional area compared to the cross-sectional area of the process flow in the inlet channel. This means in part that a smaller volume of focused process fluid occupies a given outlet channel length compared to the same length of inlet channel. This also means that a species of interest in the process flow, such as a molecule or cell of interest, may be confined to a smaller portion of the outlet channel. An advantage of the shown embodiment may be that the molecule of interest may be confined in the vertical direction to the portion of the channel occupied by the process flow so that it is confined to a subset of the vertical positions between the top and the bottom of the channel.

Figure 3:
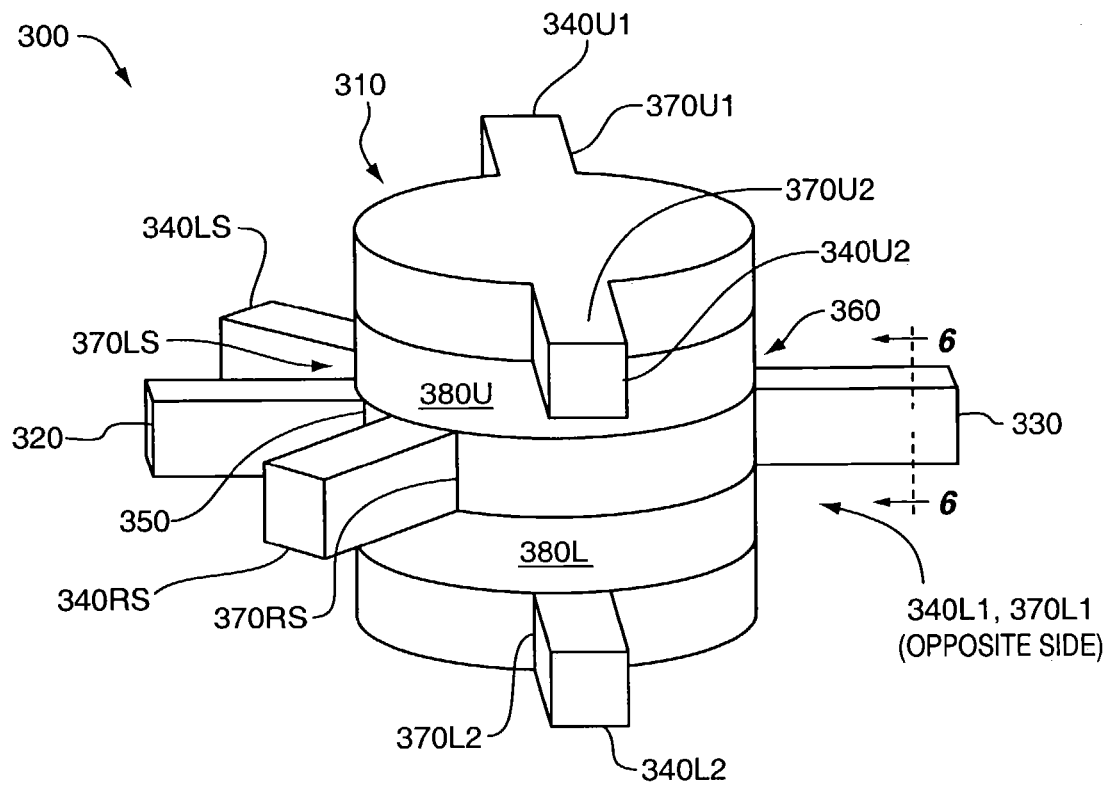
FIG. 3 shows a front perspective view of a hydrodynamic focusing device, according to another embodiment of the invention.

FIG. 3 shows a front perspective view of a hydrodynamic focusing device 300, according to one embodiment of the invention. The hydrodynamic focusing device contains a micro-fluidic inlet channel 320 to convey a process flow and a plurality of micro-fluidic focusing channels 340 (340LS, 340RS, 340U1, 340U2, 340L1, and 340L2) to each convey one of a plurality of focusing flows to focus the process flow. The hydrodynamic focusing device also contains a focusing manifold 310 coupled with the inlet channel 320 at an inlet channel port 350 and with the plurality of focusing channels 340 at a plurality of focusing channel ports 370 (370LS, 370RS, 370U1, 370U2, 370L1 and 270L2). The focusing manifold focuses the process flow by contacting all four sides thereof with the focusing flow. Still further the hydrodynamic focusing device contains a micro-fluidic outlet channel 330 coupled with the focusing manifold 310 at an outlet channel port 360 to convey the combined focused process flow and focusing flow from the focusing manifold.

The plurality of focusing channels include six channels. The six channels include a first focusing channel 340LS on a first side of the inlet channel (a left side), a second focusing channel 340RS on a second opposite side of the inlet channel (a right side), a third upper focusing channel 340U1 over the inlet channel on the first side of the focusing channel. Continuing on the six channels include a fourth upper focusing channel 340U2 over the inlet channel on the second opposite side of the focusing channel, a fifth lower focusing channel 340L1 under the inlet channel on the first side of the focusing channel (not shown), and a sixth lower focusing channel 340L2 under the inlet channel on the second side of the focusing channel. As shown it may be appropriate for the third and the fourth focusing channels, as well as for the fifth and the sixth focusing channels, to have similar or substantially equal angles relative to the inlet channel. The substantially equal angles encompass angles that differ by about 15° or less. This may help to cancel out components of momentum of the focusing flows conveyed through these channels, which are not aligned with the direction of the process flow, to cancel out within the focusing manifold, and may help avoid turning or mixing of the process flow. In the illustrated device, the third and the fourth focusing channels, as well as the fifth and the sixth focusing channels, approach the focusing manifold from opposite sides at angles that are approximately normal or orthogonal to the inlet channel, although this is not required. Also as shown, the third focusing channel may be substantially vertically aligned over the fifth focusing channel and the fourth focusing channel may be substantially vertically aligned over the sixth focusing channel. If it is appropriate to avoid tilting or turning the process flow, then it may be appropriate to maintain similar or equal flow rates in the third and the fourth focusing channels, and in the fifth and the sixth focusing channels. Alternatively, if it is appropriate to tilt or turn the process flow, then the amount of tilt or turn may be controlled by controlling different flow rates in the third and the fourth focusing channels, and in the fifth and the sixth focusing channels in order to create a net moment or force on the process flow. If desired the size of the third, fourth, fifth, and sixth focusing channels may be reduced, compared to the size of the third and fourth focusing channel shown in FIG. 4, in order to account for the additional flow capacity introduced through the addition of the fifth and sixth flow channels in the illustrated device, although this is not required. Lower flow velocities may alternatively be employed.

The focusing manifold includes the inlet port 350 to receive a process flow conveyed through the inlet channel, the outlet port 360 to provide a focused process flow to the outlet channel, and the six of focusing flow ports 370 to receive the focusing flows. Specifically, the six focusing flow ports 370 include a first port 370LS (not visible) on the first side of the inlet channel (a left side) to receive a focusing flow conveyed through the first focusing channel, a second port 370RS on a second side of the inlet channel (a right side) to receive a focusing flow conveyed through the second focusing channel, and a third upper port 370U1 over the inlet channel, on the first side of the focusing manifold, to receive a focusing flow conveyed through the third focusing channel. Continuing on, the six further include a fourth upper port 370U2 over the inlet channel, on the second side of the focusing manifold, to receive a focusing flow conveyed through the fourth focusing channel, a fifth lower port 370L1 (not shown) under the inlet channel, on the first side of the focusing manifold, to receive a focusing flow conveyed through the fifth focusing channel, and a sixth lower port 370L2 under the inlet channel, on the second side of the focusing manifold, to receive a focusing flow conveyed through the sixth focusing channel. As shown, the third upper port 370U1 may be substantially vertically aligned over the fifth lower port 370L1 (not shown) and the fourth upper port 370U2 may be substantially vertically aligned over the sixth lower port 370L2, although this is not required. Other features of the device 300 may be similar to those of the above-described device 200 shown in FIG. 2A.

Figure 4:
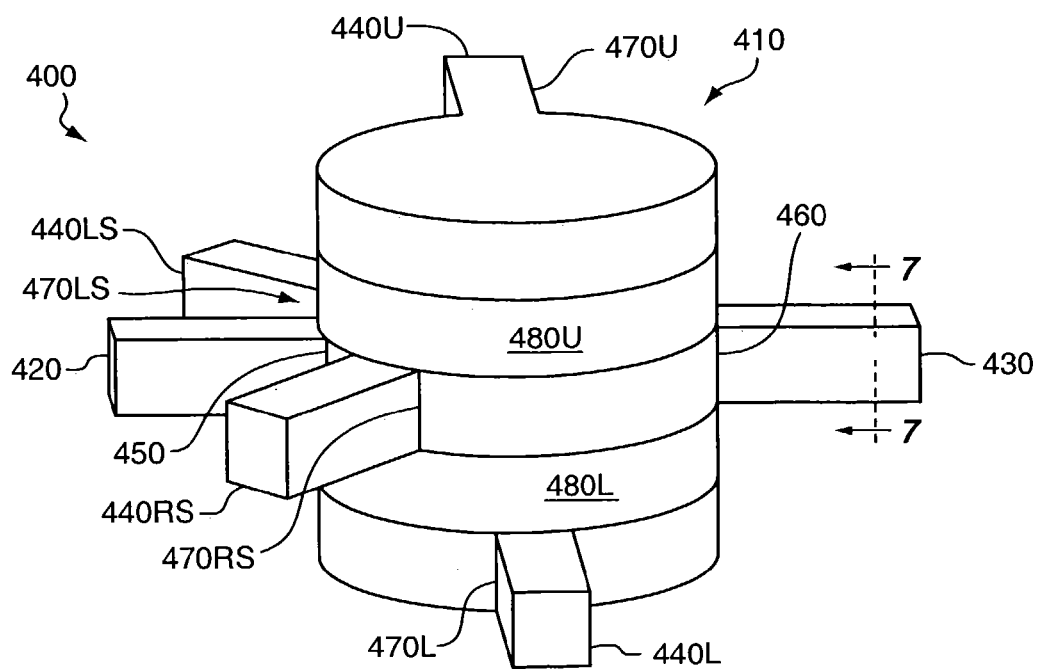
FIG. 4 shows a front perspective view of a hydrodynamic focusing device, according to yet another embodiment of the invention.

FIG. 4 shows a front perspective view of a hydrodynamic focusing device 400, according to an embodiment of the invention. The hydrodynamic focusing device 400 has features similar to the device 300 shown in FIG. 3, except for the omission of the fourth upper focusing channel 340U2 over the inlet channel on the second opposite side of the focusing channel, and the omission of the fifth lower focusing channel 340L1 under the inlet channel on the first side of the focusing channel. The focusing device contains a micro-fluidic inlet channel 420 to convey a process flow and a plurality of micro-fluidic focusing channels 440 (440LS, 440RS, 440U, and 440L) to each convey one of a plurality of focusing flows. The focusing device 400 also contains a focusing manifold 410 coupled with the inlet channel 420 at an inlet channel port 450 and with the plurality of focusing channels 440 at a plurality of focusing channel ports 470 (470LS, 470RS, 470U, and 470L) to focus the process flow by pressurized impact with focusing flow. Still further the focusing device 400 contains a micro-fluidic outlet channel 430 coupled with the focusing manifold 410 at an outlet channel port 460 to convey the combined focused process flow and focusing flow from the focusing manifold.

The four focusing channels include a first focusing channel 440LS on a first side of the inlet channel, a second focusing channel 440RS on a second opposite side of the inlet channel, a third upper focusing channel 440U over the inlet channel on the first side of the focusing channel, and a fourth lower focusing channel 440L under the inlet channel on the second side of the focusing channel. The third upper and the fourth lower focusing channels approach the focusing manifold from opposite sides of the inlet channel at angles that are approximately normal or orthogonal to the inlet channel, although this is not required. In another embodiment of the invention, the third and fourth focusing channels may have any other angle relative to the inlet channel. For example the angles may be in a range between 0° to 90° relative to the inlet channel. The manifold includes an inlet port 450 to receive a process flow conveyed through the inlet channel, an outlet port 460 to provide a focused process flow to the outlet channel, and four focusing flow ports 470, each corresponding to one of the four focusing channels, to receive the focusing flows. Specifically, the four focusing flow ports include a first port 470LS (not visible) on the first side of the inlet channel to receive a focusing flow conveyed through the first focusing channel, and a second port 470RS on a second side of the inlet channel to receive a focusing flow conveyed through the second focusing channel. Continuing on the four focusing flow ports further include a third port 470U over the inlet channel, on the first side of the focusing manifold, to receive a focusing flow conveyed through the third focusing channel, and a fourth port 470L under the inlet channel, on the second side of the focusing manifold, to receive a focusing flow conveyed through the fourth focusing channel.

Figure 7:
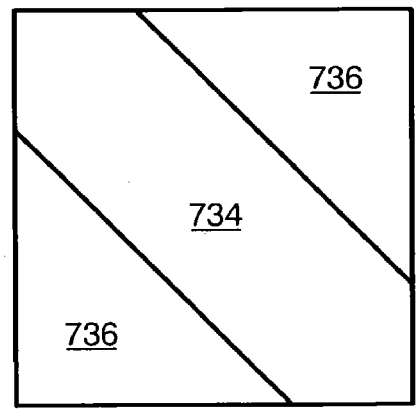
FIG. 7 shows conceptualized simulation results at a cross section of the outlet channel indicated by a section line 7—7 shown in FIG. 4, according to an embodiment of the invention.

The third and the fourth focusing flows exert net forces or moments on the fluid within the focusing manifold that turn or tilt the process flow (see e.g., FIG. 7). The third focusing flow exerts a force to push, turn, or tilt the fluid in the upper portion of the manifold fluid, including at least a portion of the process fluid, away from the first side where it enters. The fourth focusing flow exerts a force to push, turn, or tilt the lower portion of the manifold fluid, including at least a portion of the process fluid, away from the second side where it enters. The net force or moment may tilt the process flow within the focusing manifold so that an upper portion of the process flow in the outlet channel may be tilted away from the first side of the focusing manifold (away from the third focusing channel) and the lower portion of the process flow in the outlet channel may be tilted away from the second side of the focusing manifold (away from the fourth focusing channel). An alternate mirror-image device is contemplated in which the third upper and fourth lower focusing channels approach the focusing manifold from opposite the shown directions. Also an alternate embodiment is contemplated in which one of the focusing channels is omitted and the process flow is focused by contacting three sides thereof with the focusing flows provided through the three focusing channels.

III. Experimental and Simulation Results

Figure 5:
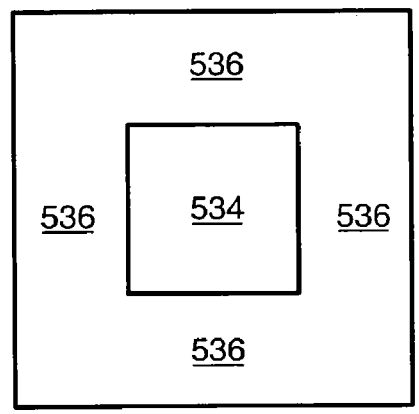
FIG. 5 shows conceptualized simulation results at a cross section of the outlet channel indicated by a section line 5—5 shown in FIG. 2, according to an embodiment of the invention.
Figure 6:
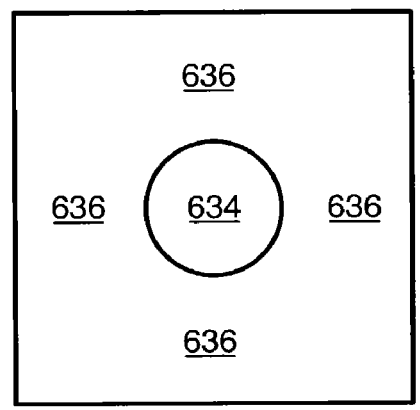
FIG. 6 shows conceptualized simulation results at a cross section of the outlet channel indicated by a section line 6—6 shown in FIG. 3, according to an embodiment of the invention.

The inventors performed simulations using Coventor-Ware™, a commercially available computational fluid dynamics software package available from Coventor Inc., of Cary, N.C. to confirm the focusing for the devices shown in FIGS. 2A, 3, and 4. Conceptualized simulation results are shown in FIGS. 5–7. The simulations assumed 100 μm width by 50 μm depth channels, an upright cylinder focusing manifold with 250 μm diameter and 250 μm height, a process flow of 10 μl/min, and a combined focusing flow of 10 μl/min divided equally among the focusing channels. Greater degree of focusing may be achieved by increasing the combined focusing flow to two, three, four, or ten times, the process flow.

FIG. 5 conceptualizes simulation results at a cross section of the outlet channel 230 of the device 200 indicated by a section line 5—5 shown in FIG. 2A and shows a focused process flow 534 and a combined focusing flow 536, according to an embodiment of the invention. As shown, the cross section of the focused process flow may have a squared shape, such as square or rectangular, with perhaps slight rounded corners. The focused process flow cross sectional area is on the order of one-half the cross sectional area of the outlet channel.

FIG. 6 shows similar results for a focused process flow 634 and a combined focusing flow 636 at a cross section indicated by a section line 6—6 shown in FIG. 3, according to an embodiment of the invention. As shown, the cross section of the focused process flow may have a rounded shape, such as circular or oval, with significant elimination of the corners. The cross sectional area of the focused process flow 634 (for device 300) may be slightly smaller compared to the cross sectional area of the focused process flow 534 (for device 200). As shown in FIGS. 5 and 6 the focused process flow is separated from all of the walls of the outlet channel, including upper and lower walls. Also, a vertical dimension or height of the focused process flow is less than a vertical dimension or height of the outlet channel.

FIG. 7 shows similar results for a focused process flow 734 and a combined focusing flow 736 at a cross section indicated by a section line 7—7 in FIG. 4, according to an embodiment of the invention. As shown, the cross section of the focused process flow may be tilted, with the top tilted away from the upper focusing channel, and with the bottom tilted away from the lower focusing channel, to give the focused process flow an angle, for example approximately 45°, in the outlet channel. Compared to those of FIGS. 5–6 the focused process flow 734 is less confined and focused along the upper right hand corner to lower left hand corner diagonal of the outlet channel.

Experiments performed on an actual focusing device of the design shown in FIG. 4 confirm the simulation results shown in FIG. 7. In the experiments the inventors used a Rhodamine 6G solution as a process flow, which fluoresces after exposure to laser radiation, and water as a focusing flow. Laser confocal microscopy was used to observe the focusing of the Rhodamine 6G solution.

IV. Forming a Focusing Device

Figure 8A:
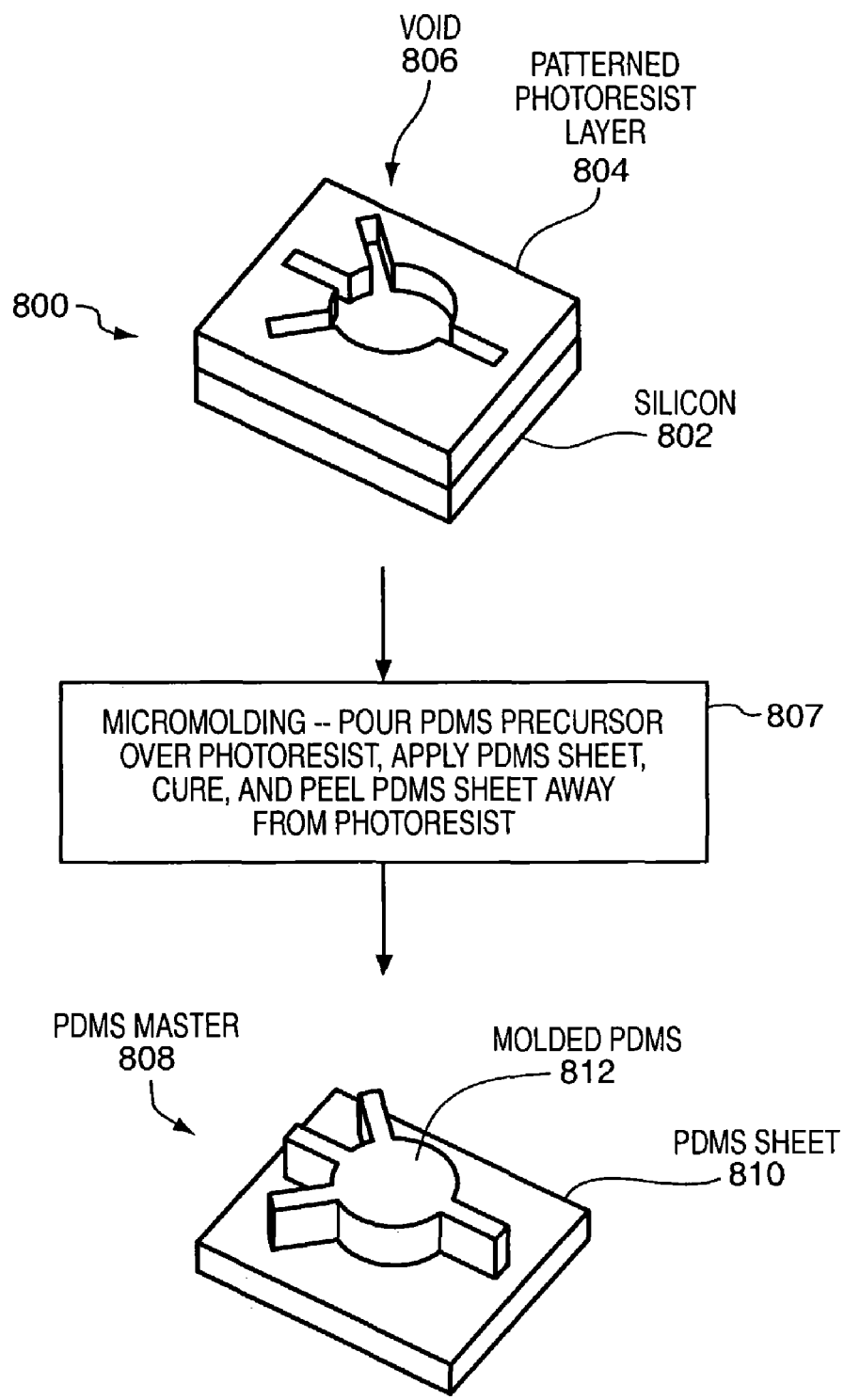
FIG. 8A–D show a method for forming a hydrodynamic focusing system by a "membrane sandwich" method, according to one embodiment of the invention.
Figure 8B:
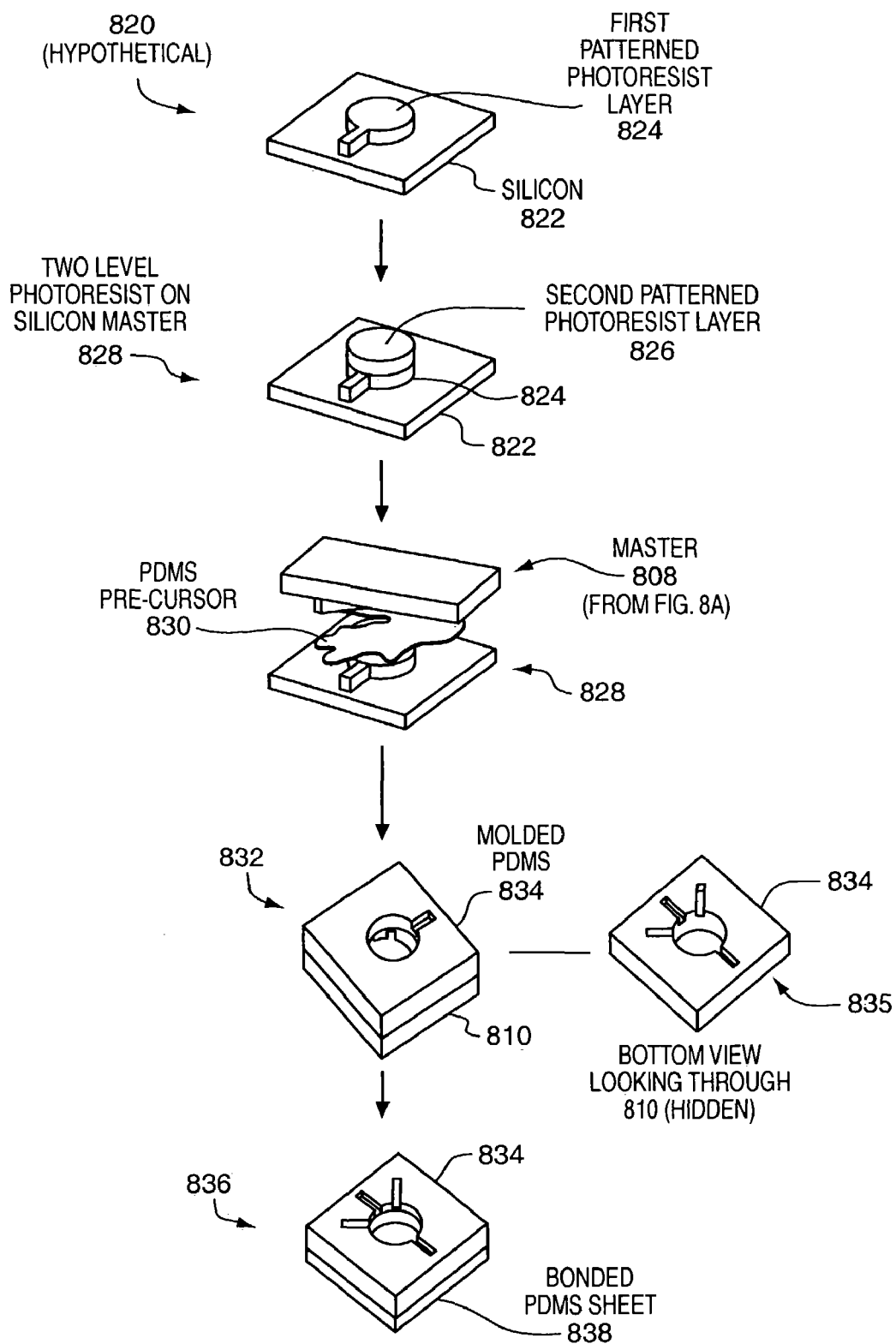
Figure 8C:
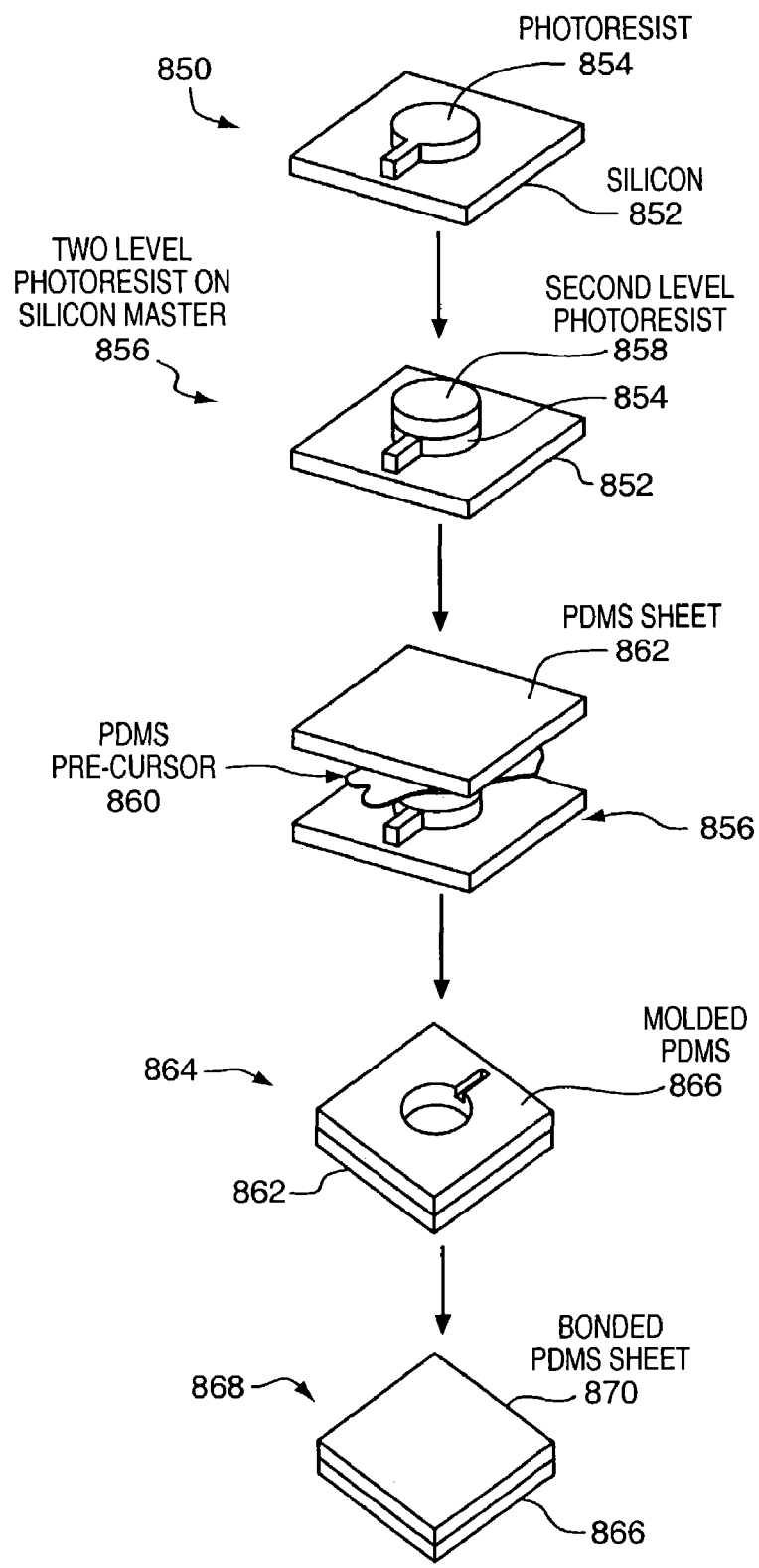

FIGS. 8A–8C show a method for forming the hydrodynamic focusing system shown in FIG. 4 by a "membrane sandwich" method, according to one embodiment of the invention. The inventors have adapted the method from the article, "*Fabrication of Topologically Complex Three-Dimensional Microfluidic Systems in PDMS by Rapid Prototyping*", by J. R. Anderson et al., published in Analytical Chemistry, Vol. 72, No. 14, published Jul. 15, 2000, pages 3158–3164.

FIG. 8A shows a method for forming a PDMS master 808 that may be used to mold a centralized portion of the hydrodynamic focusing system 400, according to one embodiment of the invention. A silicon wafer 802 measuring about 4 inches square was prepared as a support. The use of a silicon wafer is not required. The silicon wafer was singed at about 150° C. for about 30 minutes. Then, SU-8 50 photoresist was spun onto the singed silicon wafer 802 at about 2000 rpm for about 30 seconds to form a layer of photoresist on the silicon wafer 802. The layer thickness should be sufficient for the desired channel depth, for example about 50 μm. The use of this photoresist is not required and other resists or radiation sensitive layers may also optionally be employed. Then, the wafer having the photoresist layer was baked at about 65° C. for about 6 minutes, and thereafter at about 95° C. for about 20 minutes. Other temperatures and times may be appropriate for other resists.

Next, the photoresist layer was exposed through a patterned mask having a hydrodynamic focusing system pattern. Designs of the micro fluidic channels and other hydrodynamic focusing system portions were drawn to scale using a CAD program. The particular CAD program employed was Freehand 9.0, available from Macromedia of, San Francisco, Calif. The channel dimensions were about 100 μm in width and 50 μm in depth. The focusing manifold was about 250 μm in diameter and the thickness of the spacing volume layers were about 50 μm. The dimensions of the channel as well as the interconnect layers are variable and could be achieved by fabricating different sets of masters. As stated, these dimensions are illustrative and are not required. The design was then printed onto a Mylar transparency using a high-resolution printer (for example >3600 dpi). Ultraviolet (UV) light having a wavelength of about 365 nm was directed through the patterned mask to selectively expose portions of the photoresist layer. A dose of about 400 mJ/cm$^2$ was employed. Other wavelengths and doses may be appropriate for other resists.

After exposure, the wafer having the exposed photoresist was baked at about 65° C. for about 1 minute and then at 95° C. for about 5 minutes. After the post-exposure bake, the wafer was immersed in SU-8 developer for about 10 minutes in order to develop the unexposed regions. Development yielded a one-level photoresist on silicon master 800 containing a patterned photoresist layer 804 over the silicon wafer 802. The patterned photoresist layer 804 contains a void 806 that contains void portions approximately corresponding to the inlet channel 420, side focusing channels 440RS, 440LS, central portion of focusing manifold 410, and outlet channel 430. The SU-8 photoresist on the wafer was then silanized for about 1 hour by placing the wafers in proximity with a few drops of trimethylchlorosilane in a vacuum desiccator. The silanized patterned photoresist layer 804 on the silicon wafer 802 represents a lithographically patterned photoresist on silicon master 800.

The patterned photoresist on silicon master 800 was used as the master to micro-mold a master for a centralized portion of the hydrodynamic focusing system. A curable material was poured over the silanized photoresist on silicon master 800. The curable material used in this particular example was a PDMS precursor material. PDMS may offer certain advantages such as compatibility with biological materials and chemicals and transparency to facilitate alignment, although the use of PDMS is not required and other curable materials may optionally be employed. The PDMS precursor material was prepared by combining 10 parts by weight of Sylgard A with about 1 part by weight of Sylgard B. Sylgard A and B are brand silicon elastomer forming materials that are commercially available from Dow Corning of Midland, Mich. The combination was mixed thoroughly and degassed to remove any air bubbles to form the PDMS precursor. A PDMS sheet or flat slab 810 was applied to the PDMS precursor and sufficient pressure was applied to form contact without damaging or distorting features.

The PDMS precursor material on the master was cured at about 65° C. for about 2 hours. The curing solidified the PDMS precursor material as a solid PDMS material. A PDMS master 808 was carefully peeled away from the patterned photoresist on silicon master 800. The PDMS master 808 contains a patterned PDMS portion 812 corresponding to the void 806 attached to the PDMS sheet 810. The PDMS master 808 was plasma treated for about 1 minute, and then silanized for about 3 to 4 hours in proximity to a few drops of trimethylchlorosilane in a vacuum desiccator. This PDMS master 808 contains the patterned PDMS portion 812. The PDMS master may be used to mold the centralized portion of the hydrodynamic focusing system, including the inlet channel 420, the side focusing channels 440RS, 440LS, the central portion of focusing manifold 410, and the outlet channel 430.

FIG. 8B shows a method for forming an upper, two-level photoresist on silicon master 828, and then using the photoresist on silicon master 828, together with the PDMS master 808 (from FIG. 8A), to form an upper and centralized portion of the hydrodynamic focusing system 400, according to one embodiment of the invention. Initially, two-level photolithography was used to fabricate first and second patterned photoresist layers on a second silicon wafer. The second silicon wafer was singed at about 150° C. for about 30 minutes. SU-8 50 photoresist was spun over the wafer at about 2000 rpm for about 30 seconds to form a photoresist layer. The thickness was about 50 µm. The wafer having the photoresist layer was baked at about 65° C. for about 6 minutes and then at about 95° C. for about 20 minutes. The wafer was then exposed using 365 nm UV light at a dose of about 350 to 400 mJ/cm². A patterned transparency mask was used to form the patterned portion 824. A hypothetical view of a one-level photoresist on silicon mask 820 shows a patterned photoresist layer 824 over the silicon wafer 822. The patterned photoresist 824 contains portions corresponding to the upper focusing channel 440U and an upper portion of the focusing manifold 410. The view would normally not be seen since development in this method is generally not performed until after exposure of the second photoresist layer. Then, the exposed wafer was post-exposure baked at about 65° C. for about 1 minute and then at about 95° C. for about 5 minutes.

After the post-exposure bake, instead of developing, a layer of SU-8 photoresist was formed over the existing exposed and baked photoresist layer with spinning. A thickness of about 50 µm was employed to provide an interconnect between the different layers. Then, the wafer was soft-baked at about 65° C. for about 6 minutes and then at about 95° C. for about 20 minutes. Several additional minutes at each temperature may be appropriate if a thicker layer is employed, for example a 100 µm layer. Then, the wafer was exposed using a mask that contains the second level of features. The second level may form the interconnection between the different layers during the final sandwich assembly. The second level of features include a circle with a diameter of about 250 µm corresponding in position to the upper spacing volume 480U. Alignment of the features was achieved by aligning the marks in the first layer of the exposed and cross-linked photoresist with the marks in the transparency mask. After exposure, the wafers were baked at about 65° C. for about 1 min and then at about 95° C. for about 5 minutes. An additional 5 minutes at 95° C. may be appropriate for a 100 µm layer.

Then, both layers of the photoresist were developed simultaneously by immersing in SU-8 developer for about 15–20 minutes. Development yields a two-level photoresist on silicon master 828 that includes a first patterned photoresist layer 824 on a silicon wafer 822, and a second patterned photoresist layer 826 on the first patterned photoresist layer 824.

The silanized PDMS master 808 (from FIG. 8A) and the two-level photoresist on silicon master 828 were brought face-to face in the proper relative orientation (see FIG. 4) with a few drops of the PDMS precursor disposed there between. The features were aligned using a simple stereomicroscope. Sufficient pressure was applied to the top PDMS master to exude the excess precursor from between the two masters. The pressure was less than that which would deform the masters. The assembly was then cured at about 65° C. for about 1 hour. Once cured, the top PDMS master with the membrane was carefully peeled away from the two-level photoresist on silicon master 828. An intermediate assembly 832 includes molded PDMS 834 attached to the PDMS sheet 810. Immediately to the right of the intermediate assembly 832 is a hypothetical bottom view 835 of the intermediate assembly 832. The hypothetical bottom view imagines looking through the PDMS sheet 810 and molded PDMS 812 and shows the centralized portions of the hydrodynamic focusing system 400 molded from the PDMS master 808.

To facilitate removal of the molded PDMS 834 from the PDMS sheet 810 and molded PDMS 812, another thin PDMS sheet 838 was bonded to the top of the molded PDMS 834 where the two-level photoresist on silicon master 828 was removed. Plasma oxidation was used to achieve bonding and the assembly was cured at about 65° C. for about 30 minutes to improve the bonding between the plasma-treated surfaces. Then, the bonded PDMS sheet 838 and molded PDMS 834 were carefully peeled away from the initial, more weakly attached PDMS master 808 to form an intermediate assembly 836. Then reservoir holes may be punched in the PDMS slab using a standard 6 mm hole puncher.

FIG. 8C shows a method for forming a two-level photoresist on silicon master 856 and then using the master 856 to form an upper portion of the hydrodynamic focusing system 400, according to one embodiment of the invention. Initially, the two-level photoresist on silicon master 856 may be formed similarly to the two-level photoresist on silicon master 828 shown and described in FIG. 8B.

Then, a PDMS sheet 862 was used to sandwich a PDMS precursor solution 860 on top of the two-level photoresist on silicon master 856. Sufficient pressure was applied to the top PDMS sheet 862 to exude the excess precursor without deforming the PDMS. The assembly was then cured at about 65° C. for about 1 hour. Once cured, the PDMS sheet 862 with the cured molded PDMS 864 attached thereto was carefully peeled away from the two-level photoresist on silicon master 856 to form an intermediate assembly 864.

To help remove the molded PDMS 866 from the PDMS sheet 862, another PDMS sheet 870 was bonded to the molded PDMS 866 where the two-level photoresist on silicon master 856 was removed. Plasma oxidation was used to form the initial attachment and the assembly was cured at about 65° C. for about 30 minutes to improve the bonding between the plasma-treated surfaces. Then the molded PDMS 866 and bonded PDMS sheet 870 were carefully peeled away from the more weakly bonded initial PDMS sheet 862.

Figure 8D:
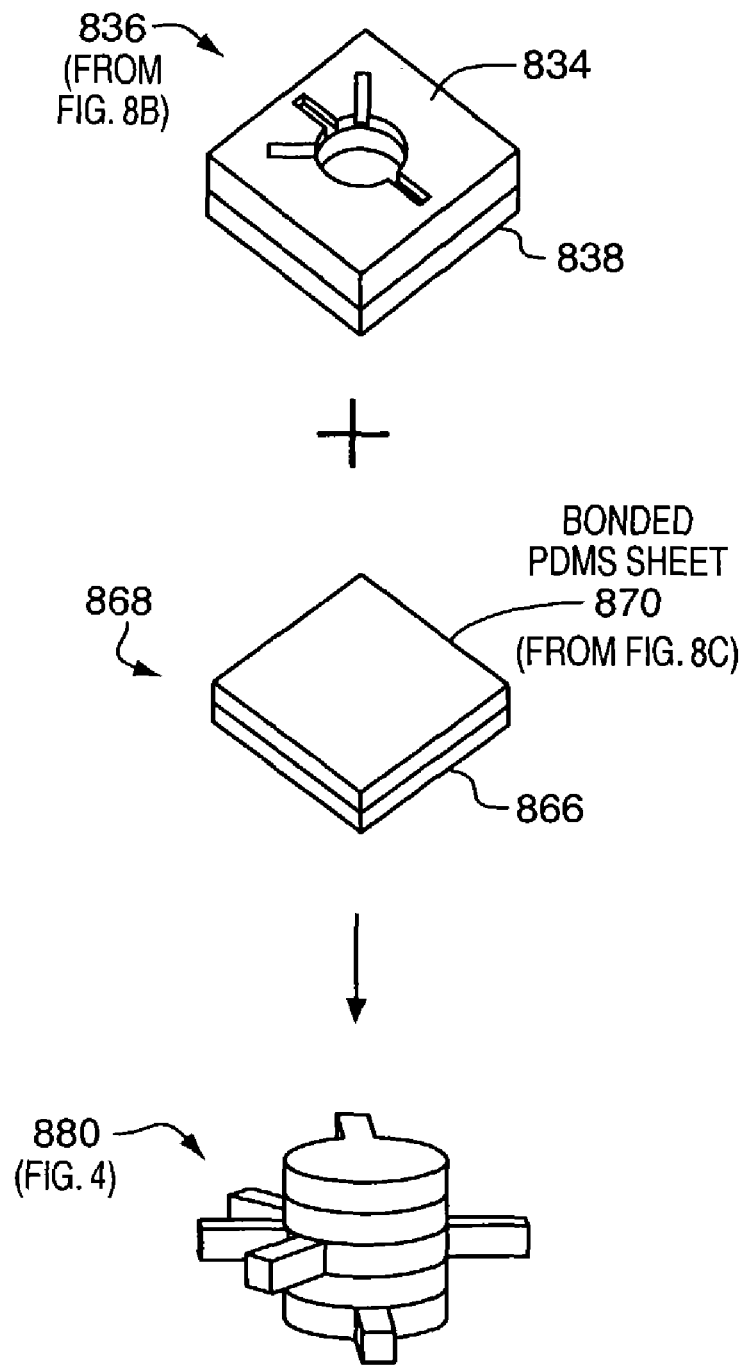

FIG. 8D shows a method for forming the hydrodynamic focusing system by bonding the intermediate assembly 836 (from FIG. 8B) containing the molded PDMS 834 and bonded PDMS sheet 838 to the intermediate assembly 868 (from FIG. 8C) containing the molded PDMS 866 and bonded PDMS sheet 870, according to one embodiment of the invention. The intermediate assemblies were placed with their molded PDMS portions facing one another and were aligned using a simple xyz stage with rotational and tilt freedoms. The orientation had the focusing channel of the molded PDMS 866 orthogonal to the inlet channel of the molded PDMS 836. The entire alignment system was placed inside a plasma chamber and was plasma treated for about 1 minute at about 100 Watts. Then, after plasma treatment, the molded PDMS portions were brought into conformal contact and cured at about 65° C. for about 30 minutes to improve bonding. The bonding of these assemblies completes the assembly of the hydrodynamic focusing system 400. As desired, syringes, tubing, or other fluid paths may be coupled with the hydrodynamic focusing system using techniques known in the arts. If desired, a transparent coverslip, such as a glass slide, may be incorporated using techniques known in the arts.

The above exemplary method of forming a hydrodynamic focusing system is to be construed as merely illustrative, rather than limiting, and to allow one skilled in the art to utilize the invention. The particular method described above is not required, and variations of the method, as well as entirely different methods may be used to form hydrodynamic focusing systems. In alternate embodiments of the invention, the focusing devices shown and described herein may be formed by various micro-machining methods (e.g., micro-milling, laser ablation, or focused ion beam milling), additive and subtractive methods (e.g., deposition and lithographic etch), various material reforming methods (e.g., molding, injection molding, stamping, hot embossing, casting, etc.), as well as combinations of these techniques (e.g., focused ion beam plus chemical vapor deposition). Any machinable, etchable, reformable, moldable, stampable, embossable, or castable material may potentially be used. Suitable materials include but are not limited to inorganic materials, such as ceramics, silicon, quartz, glass, and metals (e.g., stainless steel or aluminum), and organic materials, such as polymers. Suitable polymers include among others polycarbonate, poly(methylmethacrylate) (PMMA), poly (methylsiloxine), poly(dimethylsiloxane) (PDMS), or poly (tetrafluoroethylene) (e.g., Teflon$^R$)), and combinations of these materials. It may be appropriate to form focusing devices of polymers because these materials are inexpensive and may be injection molded, hot embossed, and cast. Although glass or quartz materials may be appropriate when organic solvents or high temperatures are used.

V. Exemplary Applications of Hydrodynamic Focusing

An embodiment of the invention may be used to vertically and horizontally focus or narrow a process flow inward from at least three or four sides thereof with the focusing flows.

An embodiment of the invention may be used to vertically focus the process flow to a vertical dimension that is less than a vertical dimension of the outlet channel with the focusing flows. The process flow vertical dimension may be customized and controlled at a value less than the vertical distance from the lower wall of the outlet channel to the upper wall of the outlet channel.

An embodiment of the invention may be used to separate or isolate at least three or four sides of a process flow from outlet channel walls with the focusing flows. In one aspect a top side and/or a bottomside of a process flow may be respectively separated from upper and lower walls of an outlet channel with the focusing flows.

An embodiment of the invention may be used to horizontally and vertically focus a process flow to a cross sectional size and/or shape with the focusing flows. As one example, a predetermined cross sectional shape and aspect ratio may be controlled by providing a predetermined pressures or flow rates in focusing channels on sides of the inlet channel and corresponding predetermined pressures or flow rates in focusing channels over and under the inlet channel.

An embodiment of the invention may be used to move or precisely position a focused process flow to virtually any desired location within an outlet channel with the focusing flows. At least one of the focusing flows may be introduced with a different pressure or flow rate and the focused process flow may be moved or positioned based on the different pressure or flow rate. As one example, a focused process flow may be moved upward in the outlet channel by increasing a flow rate or pressure of focusing flow in a focusing channel under the inlet channel. Alternatively, a focused process flow may be moved downward in the outlet channel by increasing a flow rate or pressure of focusing flow in a focusing channel over the inlet channel.

An embodiment of the invention may be used to tilt or otherwise vertically realign the focused process flow with the focusing flows.

An embodiment of the invention may be used to focus a process flow for improved sample analysis. For example, a process flow containing a biological molecule, such as a nucleic acid derivative, fluorescently labeled biological molecule, or protein, may be focused and analyzed. Further aspects will be discussed below.

An embodiment of the invention may be used to perform diffusion-based mixing of a focused process flow with a focusing flow.

An embodiment of the invention may be used to transport and precisely position single molecules or small numbers of molecules or particles in a focused process flow for nucleic acid sequencing or other applications with a focusing flow.

An embodiment of the invention may be used to perform a chemical reaction in a focused process flow. For example, an embodiment of the invention may be used to fabricate a structure, such as a wall or divider within a micro-fluidic channel, as disclosed in co-pending U.S. patent application Ser. No. 10/609322 filed on Jun. 26, 2003.

VI. Hydrodynamic Focusing in Sample Analysis

Figure 9:
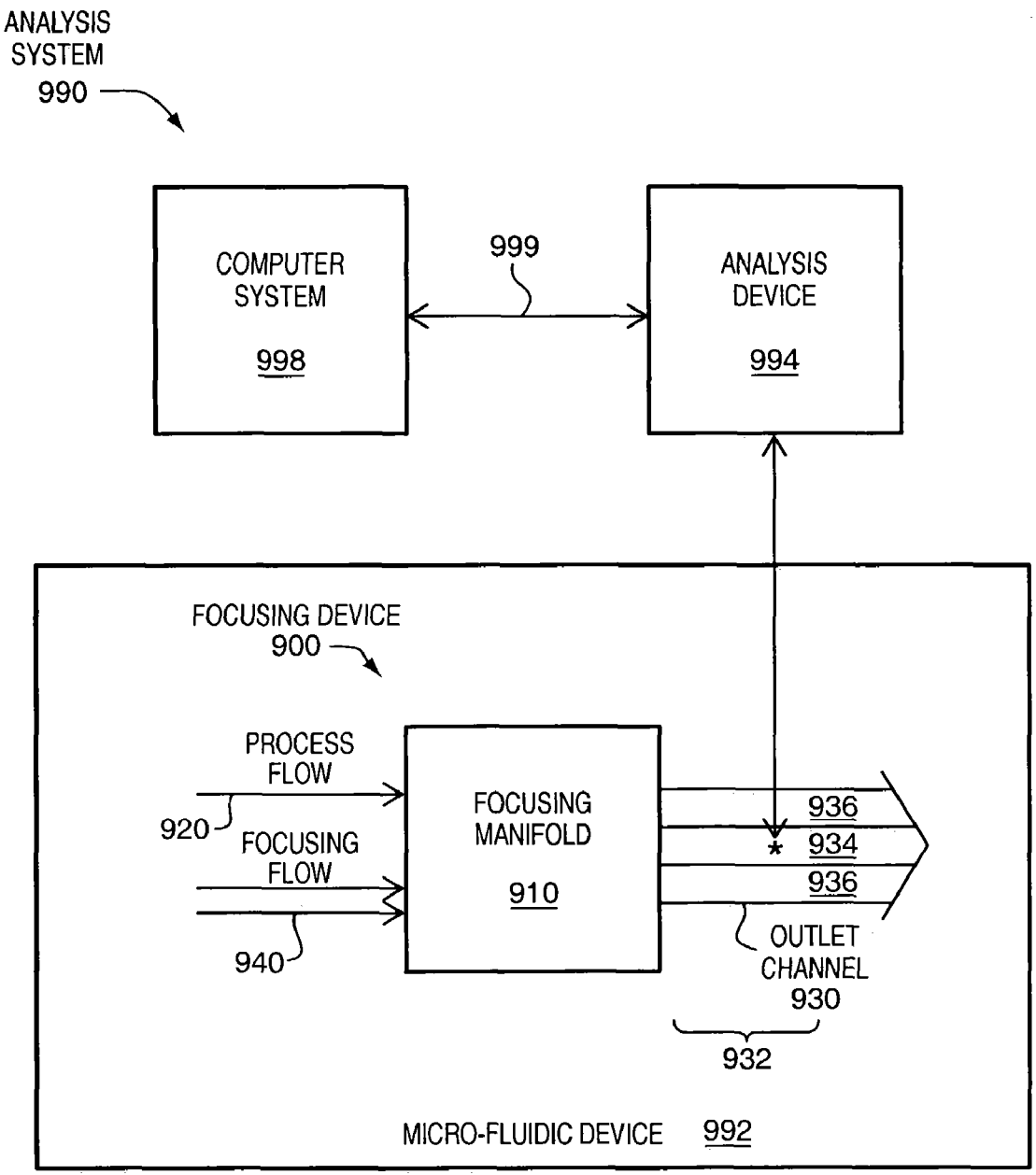
FIG. 9 shows a sample analysis system in which an embodiment of the invention may be implemented.

FIG. 9 shows a sample analysis system 990 containing an analysis device 994 to analyze a focused process flow 934 in an analysis region 932 of an outlet channel 930 of a hydrodynamic focusing device 900 residing on a micro-fluidic device 992, according to an embodiment of the invention. The hydrodynamic focusing may help to focus the process flow inward from at least three or four sides thereof, separate the focused process flow from walls of the outlet channel, reduce a cross sectional dimension or area of the focused process flow so that it is better suited for analysis, and otherwise improve sample analysis.

The sample analysis system 990 contains a micro-fluidic device 992 containing the focusing device 900. Without limitation, the micro-fluidic device 992 may comprise a small, conveniently sized, portable, hand-held, reusable or disposable micro-fluidic analysis system. The micro-fluidic device generally provides process and focusing flows to the hydrodynamic focusing system and may perform other desired operations. The process and focusing flows may be provided to the channels from an external or off-device source, such as a syringe or other fluid supply device, or an on-device source, such as a channel or other fluid passage. If an off-device fluid source is appropriate the micro-fluidic device may contain ports, for example containing a rubber or other elastomeric material, for insertion of syringe needles for the process and focusing flows.

The invention is generally not limited to any known process flow. Suitable process flows may comprise an aqueous, organic, or biological solution. The process flow may contain a species of interest 938. The species of interest may comprise a biological material, such as a cell, organelle, liposome, biological molecule or macromolecule, enzyme, protein, protein derivative, protein fragment, polypeptide, nucleic acid, DNA, RNA, nucleic acid derivative, biological molecule tagged with a particle, fluorescently labeled biological molecule, charged species, or charged protein.

The focusing device 900 contains an inlet channel 920 that receives the process flow, a plurality of focusing channels 940 that receive focusing flows, a focusing manifold 910, and an outlet channel 930. The focusing device produces a focused process flow 934 in the outlet channel. The outlet channel may contain an analysis region often located sufficiently proximate the outlet port of the focusing manifold to maintain an appropriate level of mixing due to diffusion. The focused process flow may be horizontally and vertically focused, constricted, or narrowed from at least three, or four sides thereof, by an outer focusing or sheath flow 936. The focused process flow may be centralized, not necessarily perfectly centered, and completely surrounded and confined on all sides thereof by the outer focusing or sheath flow. The focusing or sheath flow may separate the focused process flow from the outlet channel walls. This separation may be appropriate when at least a portion of the process flow may adhere to, foul, be sheared by, or otherwise be incompatible with the channel walls.

The sample analysis system also includes an analysis device 994 to analyze the focused process flow 934 in the analysis region 932 of the outlet channel. The analysis device may include a spectrometer, such as a Raman spectrometer. The Raman spectrometer may provide a coherent light from a laser, laser diode, or other light source portion to the focused process flow through a transparent material or other window of the outlet channel. The focused process flow may receive the light and inelastically scatter the light, fluoresce, or otherwise respond. The spectrometer may include a detector device portion to detect the inelastically scattered or fluoresced light. Alternatively, the analysis device may include a transistor to detect a charged species, such as a charged biological molecule, protein fragment, or cell, within the focused process flow. Other analysis devices known in the arts may alternatively be employed.

In one aspect, the focused process flow may have a cross sectional dimension or area that may be better suited for analysis. The analysis system may utilize a light beam or other signal with a smaller cross sectional dimension or area than a cross sectional dimension or area of the outlet channel. Without hydrodynamic focusing the species of interest may assume virtually any position within the entire cross section of the outlet channel and is generally not constrained to the portion of the outlet channel where the small interrogation signal or beam may be directed. As a result the species of interest may pass through the analysis region undetected. However, focusing may be advantageously employed to accurately position and focus the focused process flow containing the species of interest in a portion of the outlet channel where it may be detected with the beam. For example, the focused process flow may have a cross sectional dimension or area that is not larger than, or that is smaller than, a cross sectional dimension or area of the interrogation signal or beam. Accordingly the focusing may help improve reliability of detection of a species of interest in the process flow.

An optional computer system 998 may be used to process information associated with the analysis. As desired, a representation of the detected result may be provided to the optional computer system 998. The computer system may be programmed with instructions to analyze the representation of the detected signal. The analysis may provide an identification of a species of interest, such as an identity of a biological molecule, for example.

In an embodiment of the invention the analysis system may be used to sequence a nucleic acid and the focusing device may be used to focus a process flow containing a nucleic acid derivative in the analysis region of the outlet channel to improve detection of the nucleic acid derivative and maintain a more accurate sequence. The inlet channel may receive an aqueous solution, containing a nucleic acid derivative and potentially chemical additives. Suitable nucleic acid derivatives include but are not limited to portions of nucleic acids, nucleic acid fragments, nucleotides, nucleosides (e.g. adenosine, cytidine, guanosine, thymidine, uridine), bases (e.g. adenine, cytosine, guanine, thymine, uracil), purines, pyrimidines, or derivatives of one of these molecules.

The process flow containing the nucleic acid derivative may be provided to the focusing device and focused. Thereafter the focused process flow may be flowed to the analysis region and the analysis device may analyze the focused process flow. It may be appropriate to detect each of the nucleic acid derivatives, inasmuch as missing even one may lead to an inaccurate nucleic acid sequence. The cross sectional area of the outlet channel may be relatively large, for example 100 µm by 50 µm, compared to the cross sectional area of the analysis signal, which for example may comprise a laser beam having a diameter in the range of 0.1 µm to 50 µm, 1 µm to 10 µm, or 1 µm to 5 µm. With focusing the nucleic acid derivative may be confined within a focused process flow having a focused cross sectional dimension that related to and substantially more commensurate with a cross sectional dimension of the analysis signal or beam. For example the cross sectional dimension of the focused process flow may be not greater than, or may be less than, the cross sectional dimension of the analysis signal or beam. As an example, the focused process flow may have a cross sectional dimension that is in a range between 0.1 µm to 50 µm, 1 µm to 10 µm, or 1 µm to 5 µm in order to confine a nucleic acid derivative to a portion of the analysis region affected by a laser beam having an approximately equal diameter. Such focusing may help improve detection of nucleic acid derivatives and may help to maintain an accurate nucleic acid sequence.

VII. General Matters

In the description above, for the purposes of explanation, numerous specific details are set forth in order to provide a thorough understanding of the present invention. It will be apparent, however, to one skilled in the art that the present invention is not limited to the embodiments described, but can be practiced without some of these specific details, and can be practiced with modification and alteration within the spirit and scope of the appended claims. As an example, one or more additional focusing channels may be added to the hydrodynamic focusing systems illustrated in FIGS. 2–4 to give a total of 5, 6, 7, 10, or more focusing channels. As another example, the focusing channels may be staggered, spaced apart, or offset from one another, along the process flow direction, rather than being grouped together at a common junction, to allow serial focusing by serial introduction of focusing fluids from the offset focusing channels. As yet another example, the upper and lower focusing channels may be vertically angled or tilted at non-orthogonal angles relative to the plane of the process flow and side channels. In other instances, well-known structures, devices, and techniques have been shown in block diagram form or without detail in order not to obscure the understanding of this description. With respect to the above description then, it is to be realized that the optimum dimensional relationships for the parts of the invention, to include variations in size, materials, shape, form, function and manner of operation, assembly and use, are deemed readily apparent to one of ordinary skill in the art, and all equivalent relationships to those illustrated in the drawings and described in the specification are intended to be encompassed by the present invention.

Many of the methods are described in their most basic form, but operations can be added to or deleted from any of the methods. It will be apparent to those skilled in the art that many further modifications and adaptations can be made. The particular embodiments are not provided to limit the invention but to illustrate it. The scope of the present invention is not to be determined by the specific examples provided above but only by the claims below.

It should also be appreciated that reference throughout this specification to "one embodiment" or "an embodiment" means that a particular feature can be included in the practice of the invention. Similarly, it should be appreciated that in the foregoing description of exemplary embodiments of the invention, various features of the invention are sometimes grouped together in a single embodiment, Figure, or description thereof for the purpose of streamlining the disclosure and aiding in the understanding of one or more of the various inventive aspects. This method of disclosure, however, is not to be interpreted as reflecting an intention that the claimed invention requires more features than are expressly recited in each, claim. Rather, as the following claims reflect, inventive aspects lie in less than all features of a single foregoing disclosed embodiment. Thus, the claims following the Detailed Description are hereby expressly incorporated into this Detailed Description, with each claim standing on its own as a separate embodiment of this invention.

What is claimed is:

1. A device comprising:
a micro-fluidic inlet channel to convey a process flow;
a plurality of micro-fluidic focusing channels to each convey one of a plurality of focusing flows, wherein the plurality of focusing channels include a first channel on a first side of the inlet channel, a second channel on a second side of the inlet channel, a third upper channel over the inlet channel, and a fourth lower channel under the inlet channel, the first and second focusing channels being planar with the inlet channel and the third and fourth focusing channels being non-planar with the inlet channel;
a focusing manifold coupled with the inlet channel at an inlet port, coupled with the first channel at a first focusing channel port on a first side of the inlet channel, coupled with the second channel at a second focusing channel port on a second side of the inlet channel, coupled with the third channel at a third upper focusing channel port over the inlet channel on the first side of the inlet channel, and coupled with the fourth channel at a fourth lower focusing channel port under the inlet channel on the second side of the inlet channel, wherein the third upper focusing channel and the fourth lower focusing channel approach the focusing manifold from opposite sides thereof and are angled relative to the inlet channel with substantially equal angles, an additional upper focusing channel over the inlet channel on the second side of the inlet channel, and an additional lower focusing channel under the inlet channel on the first side of the inlet channel, wherein the additional upper focusing channel and the third upper focusing channel approach the focusing manifold from opposite sides thereof and are angled relative to the inlet channel with substantially equal angles and the additional lower focusing channel and the fourth lower focusing channel approach the focusing manifold from opposite sides thereof and are angled relative to the inlet, the focusing manifold to focus the process flow by contacting four sides of the process flow with the plurality of focusing flows; and
a micro-fluidic outlet channel coupled with the focusing manifold at an outlet channel port to convey the focused process flow and focusing flows from the focusing manifold.

2. The device of claim 1:
wherein the first and the second focusing channels are angled relative to the inlet channel with sub-orthogonal angles;
wherein the third and the fourth focusing channels approach the focusing manifold from a same side thereof as the inlet channel;
wherein the third focusing channel is substantially vertically aligned over the inlet channel and the fourth focusing channel is substantially vertically aligned under the inlet channel;
wherein the focusing manifold comprises a shape of an upright cylinder;
wherein the focusing manifold comprises an upper spacing volume between an upper focusing channel port and the inlet port; and
wherein the void volume is in a range between 0.0005 $mm^3$ to 0.01 $mm^3$.

3. A device comprising:
a micro-fluidic inlet channel to convey a process flow;
four micro-fluidic focusing channels to each convey one of a plurality of focusing flows, wherein the four micro-fluidic focusing channels comprise a first micro-fluidic focusing channel on a first side of the inlet channel, a second micro-fluidic focusing channel on a second side of the inlet channel, a third upper micro-fluidic focusing channel over the inlet channel, and a fourth lower micro-fluidic focusing channel under the inlet channel, the first and second focusing channels being planar with the inlet channel and the third and fourth focusing channels being non-planar with the inlet channel;
a focusing manifold coupled with the inlet channel at an inlet port and with the four focusing channels at a plurality of focusing channel ports to focus the process flow by contacting four sides of the process flow with the plurality of focusing flows; and
a micro-fluidic outlet channel coupled with the focusing manifold at an outlet channel port to convey the combined focused process flow and focusing flow from the focusing manifold.

4. The device of claim 3, wherein the plurality of focusing channel ports comprise a first focusing channel port on a first side of the inlet channel, a second focusing channel port on a second side of the inlet channel, a third upper focusing channel port over the inlet channel, and a fourth lower focusing channel port under the inlet channel.

5. The device of claim 3, wherein the third and the fourth focusing channels approach the focusing manifold from a same side thereof as the inlet channel.

6. The device of claim 5, wherein the third focusing channel is substantially vertically aligned over the inlet channel and the fourth focusing channel is substantially vertically aligned under the inlet channel.

7. The device of claim 3, wherein the focusing manifold comprises a shape of an upright cylinder, and wherein the void volume is in a range between 0.005 mm$^3$ to 0.01 mm$^3$.

8. The device of claim 3, wherein the focusing manifold comprises an upper spacing volume between an upper focusing channel port and the inlet port.

9. A device comprising:
a micro-fluidic inlet channel to convey a process flow;
six micro-fluidic focusing channels to each convey one of a plurality of focusing flows, wherein the six micro-fluidic focusing channels comprise a first focusing channel on a first side of the inlet channel, a second focusing channel on a second side of the inlet channel, the first and second focusing channels being planar with the inlet channel, a third upper focusing channel over the inlet channel on the first side, a fourth upper focusing channel over the inlet channel on the second side, a fifth lower focusing channel under the inlet channel on the first side, and a sixth lower focusing channel under the inlet channel on the second side;
a focusing manifold coupled with the inlet channel at an inlet port and with the six focusing channels at a plurality of focusing channel ports to focus the process flow by contacting at least four sides of the process flow with the plurality of focusing flows; and
a micro-fluidic outlet channel coupled with the focusing manifold at an outlet channel port to convey the combined focused process flow and focusing flow from the focusing manifold.

10. The device of claim 9, wherein the third upper focusing channel and the fourth upper focusing channel are on opposite sides of the focusing manifold and are angled at substantially equal angles relative to the inlet channel.

11. The device of claim 10, wherein the substantially equal angles comprise orthogonal angles.

12. The device of claim 9, wherein the third upper focusing channel is substantially vertically aligned over the fifth lower focusing channel and the fourth upper focusing channel is substantially vertically aligned over the sixth lower focusing channel.

13. The device of claim 3, wherein the third upper focusing channel is over the inlet channel on the first side of the inlet channel, and the fourth lower focusing channel is under the inlet channel on the second side of the inlet channel.

14. The device of claim 13, wherein the third upper focusing channel and the fourth lower focusing channel are on opposite sides of the focusing manifold and are angled at substantially equal angles relative to the inlet channel.

15. The device of claim 14, wherein the substantially equal angles comprise orthogonal angles.

16. A device comprising:
a micro-fluidic inlet channel to convey a process flow;
at least four micro-fluidic focusing channels to each convey one of a plurality of focusing flows, wherein the at least four micro-fluidic focusing channels include first and second focusing channels coplanar with the inlet channel, and third and fourth focusing channels not coplanar with the inlet channel, wherein the fourth micro-fluidic focusing channel is under the micro-fluidic inlet channel;
a focusing manifold coupled with the inlet channel at an inlet port, coupled with the at least four micro-fluidic focusing channels at a plurality of focusing channel ports; and
a micro-fluidic outlet channel coupled with the focusing manifold at an outlet channel port to convey the focused process flow and focusing flows from the focusing manifold.

17. The device of claim 16, wherein the third micro-fluidic focusing-channel is over the micro-fluidic inlet channel.

18. The device of claim 3, wherein the focusing manifold comprises a lower spacing volume between a lower focusing channel port and the inlet port.

19. The device of claim 3, wherein the first focusing channel and the second focusing channel are angled at substantially equal angles relative to the inlet channel.

20. The device of claim 19, wherein the angle is between 5 degrees and 90 degrees.

21. The device of claim 9, wherein the third upper focusing channel and the fourth upper focusing channel are on opposite sides of the focusing manifold and are angled at substantially equal angles relative to the inlet channel.

22. The device of claim 19, wherein the fifth lower focusing channel and the sixth lower focusing channel are on opposite sides of the focusing manifold and are angled at substantially equal angles relative to the inlet channel.

23. The device of claim 9, wherein the focusing manifold comprises a shape of an upright cylinder, and wherein the void volume is in a range between 0.005 mm$^3$ to 0.01 mm$^3$.

24. The device of claim 9, wherein the focusing manifold comprises an upper spacing volume between an upper focusing channel port and the inlet port.

25. The device of claim 9, wherein the focusing manifold comprises a lower spacing volume between a lower focusing channel port and the inlet port.

26. The device of claim 9 wherein the plurality of focusing channel ports comprise a first focusing channel port on a first side of the inlet channel, a second focusing channel port on a second side of the inlet channel, a third upper focusing channel port over the inlet channel on the first side, a fourth upper focusing channel port over the inlet channel on the second side, a fifth lower focusing channel port under the inlet channel on the first side, and a sixth lower focusing channel port under the inlet channel on the second side.

27. The device of claim 9 wherein the a micro-fluidic outlet channel is on an opposite side of the focusing manifold as the inlet channel.

28. The device of claim 9, wherein the first focusing channel and the second focusing channel are angled at substantially equal angles relative to the inlet channel.

29. The device of claim 28, wherein the angle is between 5 degrees and 90 degrees.

30. The device of claim 16, wherein the plurality of focusing channel ports comprise a first focusing channel port on a first side of the inlet channel, a second focusing channel port on a second side of the inlet channel, a third upper focusing channel port over the inlet channel, and a fourth lower focusing channel port under the inlet channel.

31. The device of claim 16, wherein the first focusing channel is on a first side of the inlet channel, the second focusing is on a second side of the inlet channel, the third focusing channel is over the inlet channel on the first side and the fourth upper focusing channel over the inlet channel on the second side.

32. The device of claim 31, wherein the third focusing channel and the fourth focusing channel are on opposite sides of the focusing manifold and are angled at substantially equal angles relative to the inlet channel.

33. The device of claim 16, further comprising fifth and sixth focusing channels not coplanar with the inlet channel, wherein the third and fourth focusing channels are above the inlet channel and the fifth and sixth focusing channels are below the inlet channel.

34. The device of claim 33, wherein the third upper focusing channel and the fourth upper focusing channel are on opposite sides of the focusing manifold and are angled at substantially equal angles relative to the inlet channel.

35. The device of claim 33, wherein the third upper focusing channel is substantially vertically aligned over the fifth lower focusing channel and the fourth upper focusing channel is substantially vertically aligned over the sixth lower focusing channel.

* * * * *